United States Patent [19]
Beuscher et al.

[11] Patent Number: 5,466,451
[45] Date of Patent: Nov. 14, 1995

[54] PHARMACEUTICALLY ACTIVE COMPOSITION EXTRACTED FROM TANACETUM PARTHENIUM, PROCESS FOR ITS EXTRACTION, AND PHARMACEUTICAL COMPOSITION CONTAINING SAME

[75] Inventors: Norbert Beuscher, Salzgitter; Ingo Willigmann, Goslar, both of Germany

[73] Assignee: Schaper & Bruemmer GmbH & Co., KG, Salzgitter, Germany

[21] Appl. No.: 11,526

[22] Filed: Jan. 29, 1993

[30] Foreign Application Priority Data

Jan. 31, 1992 [DE] Germany ............... 42 02 657.1

[51] Int. Cl.⁶ .................................................. A61K 35/78
[52] U.S. Cl. ..................... 424/195.1; 514/468; 424/450
[58] Field of Search .................... 514/468; 424/195.1

[56] References Cited

U.S. PATENT DOCUMENTS

| | | | |
|---|---|---|---|
| 4,758,433 | 7/1988 | Johnson et al. | 424/195.1 |
| 4,847,422 | 7/1989 | Klemola et al. | 568/438 |
| 4,996,317 | 2/1991 | O'Brien et al. | 544/274 |
| 5,073,267 | 12/1991 | Adda et al. | 210/634 |
| 5,196,575 | 3/1993 | Sebastian | 562/402 |

FOREIGN PATENT DOCUMENTS 98041  1/1982  European Pat. Off. ...... C07D 493/04

OTHER PUBLICATIONS

Makheja et al., "The Active Principle in Feverfew" *Lancet*, Nov. 7, 1981, p. 1054.

Rodriguez, "Ecogeographic Distribution of Secondary Constituents" in *Parthenium, Biochemical Systematics and Ecology*, vol. 5, pp. 207–218 (1977).

Brunner et al., "Zum Stand der Extraktion mit komprimierten Gasen", (on the state of extraction with compressed gases), *Chem.–Ing.–Tech.* vol. 53, No. 7, pp. 529–542 (1981).

List et al., *Technologie pflanzlicher Arzneizubereitungen* pp. 159–173, Wissenschaftliche Verlagsgesellschaft mbH, Stuttgart (1984).

R. M. Smith, et al., "Supercritical fluid extraction and gas chromatographic . . . feverfew . . . " J. Chrom. 627:225–261 1992.

Primary Examiner—Douglas W. Robinson
Assistant Examiner—Howard C. Lee
Attorney, Agent, or Firm—Foley & Lardner

[57] ABSTRACT

Extraction of pharmaceutically active compositions from a mixture of numerous ingredients, in particular from comminuted plants, such as *Tanacetum parthenium*, succeeds with a high yield and a surprisingly improved stability of the active substances when the extraction is carried out with a gas, preferably $CO_2$, in the supercritical state.

19 Claims, No Drawings

PHARMACEUTICALLY ACTIVE COMPOSITION EXTRACTED FROM TANACETUM PARTHENIUM, PROCESS FOR ITS EXTRACTION, AND PHARMACEUTICAL COMPOSITION CONTAINING SAME

BACKGROUND OF THE INVENTION

This invention relates to a pharmaceutically active composition from *Tanacetum parthenium* containing the sesquiterpene lactone parthenolide and parthenolide-like compounds as ingredients which predominate in terms of amount. The invention further relates to a process for extracting a pharmaceutically active composition from finely milled *Tanacetum parthenium* and to a medicament prepared with the resulting pharmaceutically active composition.

For the preparation of an extract from the comminuted plant *Tanacetum parthenium* EP 0 098 041 A1 describes the extraction of sesquiterpene lactone with an oil from the plant. The sesquiterpene lactone is obtained from the plant in general using a non-polar organic solvent, and light petroleum, hexane or chloroform are suitable. It is possible in this connection after the extraction with a first non-polar solvent, to evaporate the first solvent and subsequently to chromatograph the extract with a second non-polar solvent as at least the first eluent.

An article "The Active Principle In Feverfew" in *The Lancet* of Nov. 7, 1981, page 1054, discloses the preparation of an extract from the dried plant with light petroleum. A subsequent chromatography can be carried out with benzene as a polar eluent. *Biochemical Systematics and Ecology*, 1977, pages 207 to 218, describes the extraction of sesquiterpene lactones from *Tanacetum parthenium* with chloroform, that is to say with an a polar extraction agent.

It is furthermore known to carry out an extraction with a phosphate buffer solution.

It has been found that the known extraction processes produce a relatively low yield. Furthermore, the extracted sesquiterpene lactones from *Tanacetum parthenium* prove to be relatively unstable.

SUMMARY OF THE INVENTION

It is an object of the invention to provide a novel pharmaceutically active composition from *Tanacetum parthenium* and a pharmaceutical composition containing the same.

Another object of the invention is to provide pharmaceutical composition containing an extract from *Tanacetum parthenium*, which composition has improved stability.

It is also an object of the invention to provide a process for extracting a pharmaceutically active composition from *Tanacetum parthenium* in good yield.

These and other objects of the invention are achieved by providing a pharmaceutically active composition obtained from *Tanacetum parthenium* containing the sesquiterpene lactone parthenolide and parthenolide-like compounds as predominant ingredients, said composition obtained by a process comprising finely milling *Tanacetum parthenium*, and extracting the finely milled *Tanacetum parthenium* with $CO_2$ in the supercritical state at a temperature of from 32° to 60° C. and under a pressure from 150 to 350 bar.

According to a further aspect of the invention, the objects are achieved by providing a process for extracting a pharmaceutically active composition from *Tanacetum parthenium* said process comprising extracting finely milled *Tanacetum parthenium* with $CO_2$ in the supercritical state at a temperature from 32° to 60° C. and under a pressure from 150 to 350 bar.

DETAILED DESCRIPTION OF PREFERRED EMBODIMENTS

The pharmaceutically active composition according to the invention from *Tanacetum parthenium* with sesquiterpene lactone parthenolides as ingredients which predominate in terms of amount is obtainable by the following process steps:

fine milling of the plant carrying out of an extraction with $CO_2$ in the supercritical state at a temperature of from 32° to 60° C. and under a pressure from 150 to 350 bar.

The pharmaceutically active composition according to the invention differs from the extracts from *Tanacetum parthenium* which have been obtained with prior extraction processes. This is evident from the fact that the parthenolide content of the composition according to the invention remains essentially constant over a storage period of more than one year, whereas the parthenolide content of conventional extracts decreases significantly over this period. Without being bound to any theory, it is believed that the difference between the pharmaceutically active composition according to the invention and the conventional extracts from *Tanacetum parthenium* is attributable to the fact that in the conventional processes characteristic reactive groups of the sesquiterpene lactones, such as the exocyclic methylene group and the epoxide functionality, are destroyed, whereas they are retained in the composition according to the invention.

The invention also relates to a process of the initially mentioned type, in which the extraction is carried out with $CO_2$ in the supercritical state at a temperature from 32° to 60° C. and under a pressure from 150 to 350 bar. This process yields the aforementioned pharmaceutically active composition with its surprising advantages.

The extract obtained with the process according to the invention furthermore has the advantage that it is free of residual solvents and any non-volatile contaminating substances possibly present therein.

The extraction with supercritical $CO_2$ permits exhaustive extraction of the plant material, whereas this cannot be achieved with other solvents.

The extraction is preferably carried out at a temperature between 32° and 60° C. The preferred pressure range is between 150 and 350 bar. Particularly preferred parameter combinations are 60° C. and 300 to 350 bar, or 40° C. and 200 bar.

The exhaustive extraction is achieved by passing the $CO_2$ in the supercritical state cyclically over the comminuted plants. On the industrial scale, moreover, a treatment time with the supercritical gas of about three hours is applied.

The extraction of *Tanacetum parthenium* with supercritical $CO_2$ leads to a stable extract which is rich in sesquiterpene lactones, especially parthenolide. The extract yield varies between 90 and 99%, depending on the choice of the extraction conditions. The parthenolide yield is correspondingly between 11.9 and 14.4%.

The extract prepared according to the invention can be used to prepare a pharmaceutical composition or medicament. The medicament is particularly suitable for the treatment of migraine, asthma, bronchitis or arthritis.

It has been found, surprisingly, that the intrinsically lipophilic extract may also have a residual water content of about 5%. This entails polar substances derived from the plant being carried over into the extract. When the pharmaceutically active extract is encapsulated in soft gelatin capsules, polar ingredients, including terpenes and chlorophylis, may react with amino groups in the gelatin and lead to a cross-linking which prevents rapid dissolution of the gelatin casing. The ingredients responsible for the cross-linking can no longer be detected in the capsule contents after completion of the tanning of the gelatin casing but are completely bound to the capsule casing. This undesired effect can be prevented by the addition of silica gel to the finely milled plant material prior to the extracting step, preferably in amounts of 60 to 140 g per kg of finely milled plant material. An optimal added amount is about 100 g per kg of finely milled plant material. The treatment with silica gel may lead to a decrease in the extract yield.

The sesquiterpene lactones parthenolide, santamarin and reynosin which determine the efficacy can also be extracted fractionally from *Tanacetum parthenium*. This fractionation results in an extract which can be used in an oily formulation in soft gelatin capsules and shows no cross-linking.

It is known in principle to carry out extractions with compressed gases. A review of the fundamentals of this extraction process and of the principal areas of application is to be found in Brunner, Peter "Zum Stand der Extraktion mit komprimierten Gasen" in *Chem.-Ing.-Tech.* 53 (1981) pages 529 to 542. Besides the description of the fundamentals of the extraction with supercritical gases, it is evident from tables of examples of the use of such extraction processes that the main areas of application are in gas extraction for petroleum and similar products, coal, edible oils and fats and in the decaffeination of coffee. A single case, which is not explained in detail, of the use of such an extraction process for preparing a pharmaceutical is mentioned.

Extraction with supercritical gases is likewise explained in the work List, Schmidt, *Technologie pflanzlicher Arzneizubereitungen*, Stuttgart, 1984, pages 159 to 173. In this case $CO_2$ is mentioned as a preferred extraction gas. Some applications in the pharmaceutical sector are mentioned. The essential advantage indicated is that the extracts are assured to be free of solvents. There is no indication in this publication that extraction with $CO_2$ in the supercritical state results in extracts which differ from those from conventional extraction processes, or that such extracts have different properties.

The pharmaceutically active composition obtained by the extraction process according to the invention contains the sesquiterpene lactone parthenolide as the predominant ingredient in terms of amount.

The extracts obtained under the preferred operating conditions have a fat-like consistency, an intense odor and become darker as the extraction time increases. The extract is preferably immediately dissolved or suspended in one or in a combination of oils which are customarily used in pharmacy. The solution is particularly suitable for use in soft gelatin capsules. However, other formulations are also possible.

In comparative pharmacological experiments, the extract obtained in the manner described above exhibited antiinflammatory and spasmolytic properties which were superior to those obtained with extracts obtained by other forms of extraction. Physicochemical parameters of the extraction and of the extract are shown in the following Table 1:

TABLE 1

| Experiment | 2 | 3 |
| --- | --- | --- |
| Extraction Parameters | 350 bar/60° C. | 200 bar/40° C. |
| Color | dark olive green | olive green |
| Consistency | grease-like | grease-like |
| Odor | characteristically aromatic | characteristically aromatic |
| Capillary Melting Point | 44–47° C. | 43–47° C. |

The following examples illustrate the obtaining of the extract on an industrial scale:

EXAMPLE 1

3.2 kg of finely milled plant material from *Tanacetum parthenium* were introduced into a ten liter extractor which was equipped for temperature and pressure control. After the apparatus was closed, gaseous $CO_2$ from the reservoir tank was brought to supercritical values, introduced into the system and then continuously pumped round in circulation. This procedure was repeated cyclically over a period of 3 hours at a pressure of 350 bar and a temperature of 60° C. until the plant material had been exhaustively extracted.

Extract yield: 99.9 g

Parthenolide yield 11.4 g

Parthenolide content of the extract: 11.4%

Residual parthenolide in extracted plant material: 0.9 g

EXAMPLE 2

3.1 kg of finely milled plant material from *Tanacetum parthenium* were introduced into a ten liter extractor which was equipped for temperature and pressure control. After the apparatus was closed, gaseous $CO_2$ from the reservoir tank was brought to supercritical values, introduced into the system and then continuously pumped round in circulation. This procedure was repeated cyclically over a period of 3 hours at a pressure of 200 bar and a temperature of 40° C. until the plant material had been exhaustively extracted.

Extract yield: 90.1 g

Parthenolide yield: 11.9 g

Parthenolide content of extract: 13.2%

Residual parthenolide in extracted plant material: 1.1 g

The extraction with supercritical $CO_2$ results not only in a considerably higher yield for the extracts, but also in a considerably greater stability of the active substances. The following Table 2 shows a comparison of the parthenolide contents of a conventional aqueous ethanolic extract and a $CO_2$ extract according to the invention over a storage time of up to about 1½ years:

TABLE 2

| | Aqueous Ethanolic Extract | | Supercritical $CO_2$ Extract | |
| --- | --- | --- | --- | --- |
| Storage Time (Days) | Parthenolide mg/g DR | % of Starting Value | Parthenolide mg/g DE | % of Starting Value |
| 0 | 8.26 | 100.0 | 119.7 | 100.0 |
| 5 | 5.81 | 70.3 | — | — |
| 7 | 7.48 | 90.6 | — | — |
| 8 | 5.60 | 67.8 | — | — |
| 20 | 3.08 | 37.3 | — | — |
| 26 | 2.34 | 28.3 | — | — |
| 32 | 1.92 | 23.2 | — | — |

TABLE 2-continued

| | Aqueous Ethanolic Extract | | Supercritical $CO_2$ Extract | |
|---|---|---|---|---|
| Storage Time (Days) | Parthenolide mg/g DR | % of Starting Value | Parthenolide mg/g DE | % of Starting Value |
| 35 | 1.63 | 19.7 | — | — |
| 47 | 1.39 | 16.8 | — | — |
| 54 | 1.22 | 14.8 | — | — |
| 126 | — | — | 111.3 | 93.0 |
| 132 | 1.05 | 12.7 | — | — |
| 313 | — | — | 116.9 | 97.7 |
| 576 | — | — | 117.2 | 97.9 |
| 587 | — | — | 123.5 | 103.2 |

DR = dry residue; DE = dry extract.

It is evident from the data in Table 2 that there is a considerable decrease in the percentage parthenolide content in the aqueous ethanolic extract, whereas the parthenolide content remains virtually constant in the $CO_2$ extract.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A pharmaceutical composition having improved stability comprising a pharmaceutically acceptable carrier in combination with an extract obtained from *Tanacetum parthenium* containing sesquiterpene lactone parthenolide compounds, said extract obtained by a process consisting essentially of:

a.) finely milling *Tanacetum parthenium*;

b.) extracting the finely milled *Tanacetum parthenium* with $CO_2$ in the supercritical state at a temperature of from 32° to 60° C. and under a pressure from 150 to 350 bars; and c.) isolating the extract thereof.

2. The pharmaceutical composition according to claim 1, obtained by extracting finely milled *Tanacetum parthenium* with supercritical $CO_2$ at a temperature of 50° C. and under a pressure of from 300 to 350 bar.

3. The pharmaceutical composition according to claim 1, obtained by extracting finely milled *Tanacetum parthenium* with supercritical $CO_2$ at a temperature of 40° C. and under a pressure of 200 bar.

4. The pharmaceutical composition according to claim 1, obtained by a process further consisting essentially of the step of adding silica gel, in an amount sufficient to bind polar substances of the *Tanacetum parthenium* to the finely milled *Tanacetum parthenium*, prior to the extracting step.

5. The pharmaceutical composition according to claim 4, wherein from 60 to 140 g of silica gel is added per kg of finely milled *Tanacetum parthenium*.

6. The pharmaceutical composition according to claim 5, wherein about 100 g of silica gel is added per kg of finely milled *Tanacetum parthenium*.

7. The pharmaceutical composition according to claim 1, obtained by a process further consisting essentially of the step of fractionating the extract obtained as a product of said extracting step to recover the sesquiterpene lactones parthenolide, santamarin and reynosin.

8. A process for extracting a pharmaceutical extract from *Tanacetum parthenium*, said process comprising extracting finely milled *Tanacetum parthenium* with $CO_2$ in the supercritical state at a temperature from 32° to 60° C., under a pressure of from 150 to 350 bars and isolating the extract thereof.

9. The process according to claim 8, wherein the extracting is carried out at a temperature of 60° C. and under a pressure from 300 to 350 bar.

10. The process according to claim 8, wherein the extracting is carried out at a temperature of 40° C. and under a pressure of 200 bar.

11. The process according to claim 8, wherein supercritical $CO_2$ is passed cyclically over the finely milled *Tanacetum parthenium*.

12. The process according to claim 11, wherein cyclic passage of supercritical $CO_2$ is carried out up to exhaustive extraction.

13. The process according to claim 8, further comprising the step of adding silica gel, in an amount sufficient to bind polar substances of the *Tanacetum parthenium* to the finely milled *Tanacetum parthenium*, prior to the extracting step.

14. The process according to claim 13, wherein from 60 to 140 g of silica gel is added per kg of finely milled *Tanacetum parthenium*.

15. The process according to claim 14, wherein about 100 g of silica gel is added per kg of finely milled *Tanacetum parthenium*.

16. The process according to claim 8, further comprising the step of fractionating the extract obtained as a product of said extracting step to recover the sesquiterpene lactones parthenolide, santamarin and reynosin.

17. A pharmaceutical composition comprising an extract of *Tanacetum parthenium* obtained by the process of claim 8 dissolved or suspended in a pharmaceutically acceptable oil.

18. A pharmaceutical composition comprising an extract of *Tanacetum parthenium* obtained by the process of claim 13 in a soft or hard gelatin capsule.

19. The process according to claim 8, wherein the extraction consists essentially of using supercritical carbon monoxide without other extracting agents.

\* \* \* \* \*